United States Patent [19]

Schülein et al.

[11] Patent Number: 5,610,048
[45] Date of Patent: Mar. 11, 1997

[54] XYLANASE, DNA SEQUENCES, CODING FOR THE XYLANASES AND METHODS OF USE THEREOF

[75] Inventors: Martin Schülein, København; Torben Halkier, Frederiksberg; Hans P. Heldt-Hansen; Henrik Dalbøge, both of Virum; Lars S. Pedersen, Lyngby, all of Denmark

[73] Assignee: Novo Nordisk A/S, Bagsvaerd, Denmark

[21] Appl. No.: 119,169

[22] PCT Filed: Mar. 27, 1992

[86] PCT No.: PCT/DK92/00099

§ 371 Date: Sep. 21, 1993

§ 102(e) Date: Sep. 21, 1993

[87] PCT Pub. No.: WO92/17573

PCT Pub. Date: Oct. 15, 1992

[30] Foreign Application Priority Data

Apr. 2, 1991 [EP] European Pat. Off. .............. 91610027

[51] Int. Cl.⁶ ............................ C12N 9/42; C12N 15/56; C12N 15/80
[52] U.S. Cl. ................... 435/209; 435/69.1; 435/252.1; 435/252.3; 435/254.3; 435/278; 536/23.2; 935/14; 935/28; 935/66; 935/68; 935/69
[58] Field of Search ................... 435/200, 209, 435/278, 69.1, 252.3, 320.1, 252.33, 252.1, 254.3, 23.2; 536/23.2

[56] References Cited

U.S. PATENT DOCUMENTS 4,652,639 3/1987 Stubinsky .............................. 435/69.1
5,116,746 5/1992 Bernier et al. ........................ 435/172.3

FOREIGN PATENT DOCUMENTS 0305216   3/1989  European Pat. Off. .
4017150   12/1991 Germany .
WO90/01060 2/1990 WIPO .
WO91/02839 3/1991 WIPO .
WO91/02791 3/1991 WIPO .

OTHER PUBLICATIONS

T. Hamamoto et al., Agric. Biol. Chem., vol. 51, No. 11, pp. 3133–3135, 1987.
A. Iwasaki et al., Journal of Antibiotics, vol. 49, No. 7, pp. 985–993, 1986.
H. Zappe et al., Nucleic Acids Research, vol. 18, No. 8, pp. 2179, 1990.
Kitpreechavanich et al., Chemical Abstracts, vol. 101, No. 25, Abstract No. 225520y, 1984.
Y. Isshiki et al., Chemical Abstracts. vol. 99, No. 23, Abstract No. 193693d, 1983.
Fortkamp, E., et al, 1986, DNA, 5(6):511–517.
Dalbøge, H., et al., 1994, Molecular and General Genetics, 243:253–260.
Pilnik, W., et al., 1990, Food Biotechnology, 4(1):319–328.
Ghangas, G. S., et al., 1989, Journal of Biotechnology, 171(6):2963–2969.
Fukusaki et al. (1984) Febs Lett. 171(2), 197–201.
Yang et al (1988) Nuc. Acids Res 16(14), 7187.

Primary Examiner—Robert A. Wax
Assistant Examiner—William W. Moore
Attorney, Agent, or Firm—Steve T. Zelson, Esq.; Elias J. Lambiris, Esq.

[57] ABSTRACT

The xylanase is characterized by several partial amino acid sequences and is immunoreactive with an antibody raised against a purified xylanase derived from *Humicola insolens*, DSM 1800. This xylanase preparation is practically free of cellulase xylanase and is well suited for treatment of paper pulp, as a baking agent and as an additive to fodder.

31 Claims, 2 Drawing Sheets

XYLANASE, DNA SEQUENCES, CODING FOR THE XYLANASES AND METHODS OF USE THEREOF

CROSS-REFERENCE TO RELATED APPLICATIONS

This application is a continuation of PCT/DK92/00099 filed Mar. 27, 1992, which is incorporated herein by reference.

The invention comprises a xylanase, a corresponding recombinant DNA sequence, a vector, a transformed host, a method for production of the xylanase, an agent containing the xylanase, and a use of the agent.

Xylan, a major component of plant hemicellulose, is a polymer of D-xylose linked by β-1,4-xylosidic bonds. Xylan can be degraded to xylose and xylo-oligomers by acid or enzymatic hydrolysis. Enzymatic hydrolysis of xylan produces free sugars without the by-products formed with acid (e.g. furans).

There are currently five major applications for xylanases; 1) enzymatic breakdown of agricultural wastes for production of alcohol fuels; 2) enzymatic modification of animal feeds or feed components or addition to animal feeds for in vivo breakdown of the hemicellulose fraction; 3) use as a baking agent; 4) manufacturing of dissolving pulps yielding cellulose; and 5) bio-bleaching of wood pulp. [Detroym R. W. In: *Organic Chemicals from Biomass*, (CRC Press, Boca Raton, Fla., 1981) 19–41.; Paice, M. G., and L. Jurasek. *J. Wood Chem. Technol.* 4: 187–198.; Pommier, J. C., J. L. Fuentes, G. Goma. *Tappi Journal* (1989): 187–191.; Senior, D. J., et al., *Biotechnol. Letters* 10 (1988):907–912.]

The pulp and paper industry is using xylanase compositions in the bleaching process to enhance the brightness of bleached pulps, to decrease the amount of chemicals used in the bleaching stages, and to increase the freeness of pulps in the recycled paper process [Eriksson, K. E. L., *Wood Science and Technology* 24 (1990); 79–101.; Paice, M. G., R. Bernier, and L. Jurasek, *Biotechnol. and Bioeng.* 32 (1988): 235–239.; Pommier, J. C., J. L. Fuentes, and G. Goma, *Tappi Journal* (1989): 187–191.]

Kraft pulping, a process widely used in the pulp and paper industry, involves the alkaline sulfate cooking of pulp to remove 90–98% of the lignin. The remaining 2–10% of lignin gives the pulp a dark brown color which has the tendency to darken in UV light or by oxidation. In order to obtain a white pulp for high quality paper, the brown color is removed by a multi-stage bleaching process using chemicals, e.g. chlorine, chlorine dioxide, ozone, oxygen or hydrogen peroxide.

Presently, there is much concern about the environmental impact of the chemicals generated from the bleaching process. Enzymes can aid in the removal of lignin from the pulp without any harmful side products. Reports show that lignin in wood is linked to xylan [Eriksson, O., et al., *Wood Sci. Technol.* 14 (1980); 267.; Takashi, N., and T. Koshijiima, *Wood Sci. Technol.* 22 (1988); 177–189]. By a limited hydrolysis of the xylan a greater release of lignin occurs during bleaching. Thus, by enzymatically treating the pulp prior to bleaching the amount of bleaching chemicals needed would in turn decrease. [Viikari, L., et al., *Proceedings of the 3rd International Symposium on Biotechnology in the Pulp and Paper Industry* (1986); 67.]

According to the technical literature, good results have been obtained by means of fungal preparations from *Trichoderma* [Paice, M. G., L. Jurasek, *J. Wood Chem. Technol.* 4 (1989): 187–198.; Senior, D. J., et al., *Biotechnol. Letters.* 10 (1988): 907–912], which require pH adjustment of the wood pulps below pH 6.0.

A Trichoderma xylanase preparation, Pulpzyme™ HA (commercially available from Novo Nordisk A/S) can be used for delignification of kraft pulps at pH 5–7. At 50° C. and pH higher than 7, the enzyme shows only little effect.

Also a *Bacillus pumilus* xylanase preparation, Pulpzyme HB (commercially available from Novo Nordisk A/S) can be used for delignification of Kraft pulps at pH 5–7. At 50° C. and pH higher than 7, the enzyme shows only little effect.

*Humicola insolens* xylanases have been described (Yoshioka, H. et al., *Agric. Biol. Chem.* 43(3) (1981) 579–586). In the crude preparation they have a pH-optimum of 6.0 and a temperature optimum of 60° C. At pH 9 they show 25% of the activity at pH 6. According to the information in the article the enzymes were not purified and will therefore contain significant cellulase activity, as *H. insolens* is known as a good cellulase producer, reference being made to U.S. Pat. No. 4,435,307. Further the enzymes are not characterized with respect to cellulases. $M_w$, pI or amino acid composition and has not been tested on kraft pulps, in baking or for animal feed.

The prior art xylanase preparation from *Humicola insolens* YH-8 described in Agric. Biol. Chem. and the other prior art xylanase preparations indicated above are not as well suited for use in delignification of kraft pulp, partly due to the relatively high cellulase content.

Thus, it is the purpose of the invention to provide a xylanase, which can be produced as a preparation with very small amounts of other enzyme activities, especially cellulase activities and other xylanase activities, and which is well suited for use in delignification of kraft pulp, as a baking agent and as an additive to animal fodder.

Figure 1:
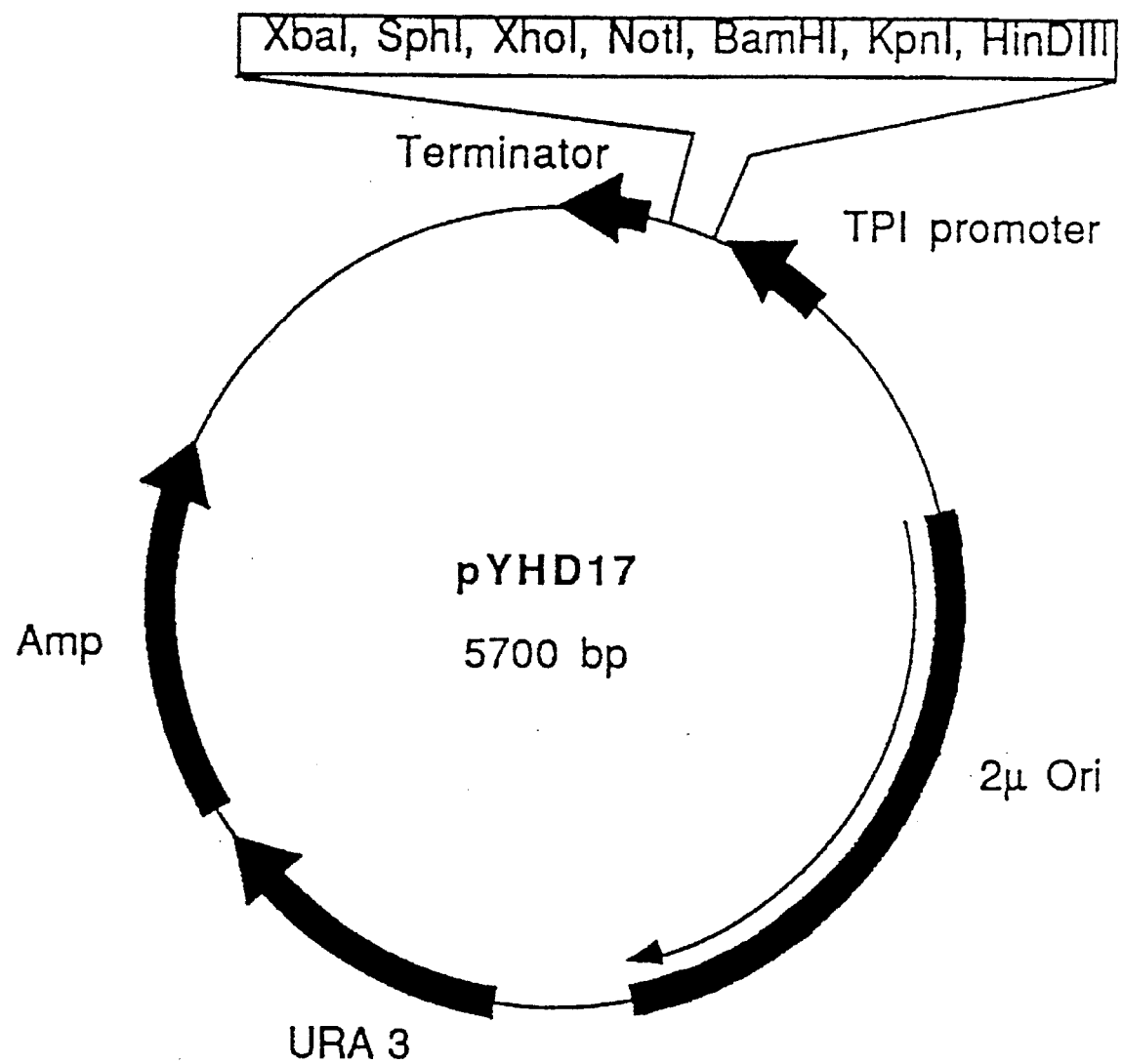
FIG. 1 depicts a functional map of the yeast expression plasmid pYHD 17 featuring a multiple cloning site positioned between the yeast TPI gene transcriptional promoter and terminator.

The xylanase according to the invention is characterized by the fact that it has the following partial amino acid sequences 1   Asn-Thr-Gly-Asn-Phe-Val-Gly-Gly-Lys-Gly-Trp-Asn-Pro-Gly-Thr-Gly-Arg-Thr-Ile-Asn-Tyr- (SEQ ID NO. 1),
2 Thr-Arg-Asn-Pro-Leu-Val-Glu-Tyr-Tyr- (SEQ ID NO. 2),
3   Ser-Trp-Trp-Ser-Asp-Gly-Gly-Gly-Gln-Val-Gln-Tyr- (SEQ ID NO. 3),
4 Val-Ser-Thr-Arg-Tyr-Asn-Gln-Pro-Ser-Ile-Asp-Gly-Thr-Arg-Thr-Phe-Gln-Gln-Tyr-Trp-Ser-Ile-Arg-Lys- (SEQ ID NO. 4),
5   Tyr-Val-Ile-Glu-Ser-Tyr-Gly-Thr-Tyr-Asn-Pro-Gly-Ser-Gln-Ala-Gln-Tyr-Lys-Gly-Thr-Phe-Tyr-Thr-Asp-Gly-Asp-Gln-Tyr-Asp- (SEQ ID NO. 5), and
6 Gln-Val-Thr-Pro-Asn-Ala-Glu-Gly-Trp-His-Asn-Gly-Tyr-Phe-Tyr- (SEQ ID NO. 6),
or a partial amino acid sequence with a homology thereto of at least 80%, preferably at least 90%.

Surprisingly, it has been found that it is possible to produce the xylanase according to the invention as part of a xylanase preparation, which contains enzymatic activities, e.g. cellulases besides xylanase in very small concentrations. Especially, it has to be noted that the xylanase according to the invention is a special xylanase selected among the several xylanases produced inherently from *Humicola insolens*, DSM 1800, which is excellently suited both as an agent for addition to paper pulp, as a baking agent and as an additive to animal fodder. Also, it has been found that the xylanase according to the invention exhibits a specific activity which is larger than the specific activity of any of the prior art xylanases. It is most surprising that the xylanase according to the invention exhibits superior properties in relation to all these technical areas, which are otherwise unrelated to each other.

The xylanase according to this invention exhibits a significant effect in removal of lignin from pulp at pH 8, as will be demonstrated later. The lignin removing effect is significantly higher than prior art (*B. pumilus*), as will be shown later.

The high performance in regard to lignin removal is surprisingly obtained with xylanase according to the invention alone, even though it is one out of several xylanase components in *H. insolens*. The process for lignin removal is more economical as only one xylanase component is needed, a component which by genetic engineering can be produced in high yields.

Surprisingly it is possible to produce the xylanase according to the invention without significant cellulase activity, thereby avoiding yield loss caused by cellulolytic attack on the cellulose fibres in the pulp during the use of the xylanase for lignin removal.

As will be shown later the xylanase according to the invention surprisingly can remove more lignin from softwood than the *B. pumilus* xylanase even though the two xylanases have very similar pH profiles.

Xylanase (the designation pentosanase is commonly used in the baking industry) is used as a baking agent for wheat bread for several purposes:
 dough development
 improving dough elasticity and stability
 increasing bread volume
 improving crumb structure
 anti-staling It is believed that some xylanases degrade the pentosans (arabinoxylans) in such a way that the thereby modified pentosans improve dough elasticity, stability and development. Surprisingly the xylanase according to the invention can modify the pentosans in such a way. The xylanase according to the invention can be produced without other xylanases and xylan modifying enzymes and thereby makes it possible to obtain a controlled modification of the pentosans.

The pH in dough is 6.0 to 5.5 which makes this xylanase ideal for the use as a baking agent, as the pH optimum of the xylanase according to the invention is 5.5 to 7.5.

The xylanase according to the invention can also be used for modification of animal feeds or for addition to animal feeds for in vivo breakdown of the hemicellulose fraction. The xylanase according to the invention can be used as a preparation with practically no side activities, whereas the prior art xylanase, represented by an *H. insolens* xylanase product, would contain several side activities, including other xylanases. It was found that the xylanase according to the invention and the prior art xylanase gave rise to similar effects in regard to weight gain in a chicken feeding trial. This shows that the xylanase according to the invention is the active or one of the active *H. insolens* xylanases in relation to the feed additive application. Furthermore, the xylanase according to the invention exhibits the significant advantage that it contains a very pure xylanase, whereby a reproducible weight gain can be obtained, in contradistinction to the prior art xylanase, which contains many different side activities with varying proportions from batch to batch. Also, use of the xylanase according to the invention, which is a single component xylanase, opens up the possibility of a more economic feed additive.

A preferred embodiment of the xylanase according to the invention is characterized by the fact that the xylanase is immunoreactive with an antibody raised against a purified xylanase derived from *Humicola insolens*, DSM 1800.

A preferred embodiment of the xylanase according to the invention is characterized by the fact that the xylanase has an isoelectric point of 7.5–9.5, preferably 8.0–8.5.

A preferred embodiment of the xylanase according to the invention is characterized by the fact that the xylanase exhibits a specific activity above 330 EXU/mg of protein, preferably above 400 EXU/mg of protein. The EXU xylanase activity unit is defined in AF 293.9/1. This AF publication and other AF publications indicated in this specification are available on request from Novo Nordisk A/S, Novo Allé, DK-2880 Bagsvaerd, Denmark.

Also, the invention comprises a recombinant DNA sequence, which is characterized by encoding for the xylanase according to the invention.

A preferred embodiment of the recombinant DNA sequence according to the invention is characterized by the fact that it comprises the following partial DNA sequence

```
         1                   5                  10                  15
        ATG GTC TCG CTC AAG TCT GTC CTC GCG GCC GCC ACG GCT GTG AGC 20                  25                  30
        TCT GCC ATT GCT GCC CCT TTT GAC TTC GTT CCT CGG GAC AAC TCG 35                  40                  45
        ACG GCC CTT CAG GCT CGC CAG GTG ACC CCC AAC GCC GAG GGC TGG 50                  55                  60
        CAC AAC GGC TAC TTC TAC TCG TGG TGG TCC GAC GGC GGA GGC CAG 65                  70                  75
        GTT CAG TAC ACC AAC CTC GAG GGC AGC CGC TAC CAG GTC AGA TGG 80                  85                  90
        NNN AAC ACC GGC AAC TTC GTC GGT GGT AAG GGT TGG AAC CCG GGA 95                 100                 105
        ACC GGC CCC ACG ATC AAC TAC GGC GGC TAC TTC AAC CCC CAG GGC
```

```
                    110                115                 120
AAC GGC TAC CTG GCC GTC TAC GGC TGG ACC NNN AAC CCG CTC GTC 125                130                  135
GAG TAC TAT GTC ATC GAG TCG TAC GGC ACG TAC AAT CCC GGC AGC 140                145                  150
CAG GCT CAG TAC AAG GGC ACA TTC TAT ACC GAC GGC GAT CAG TAT 155                160
GAC ATC TTT GTG AGC ACC CGT NNN AAC CAG CCC AGC ATC
```

A preferred embodiment of the recombinant DNA sequence according to the invention is characterized by the fact that it comprises a DNA sequence selected from a) the *Humicola insolens* xylanase DNA insert in pHD450 b) a DNA sequence which hybridizes to the coding region for the mature xylanase DNA comprised by the DNA insert of a) and which comprises a structural gene for a polypeptide with xylanase activity, and optionally a promoter, a coding region for a signal or leader peptide and/or transcriptional terminator c) a DNA sequence with a homology sufficient to hybridize to the sequence indicated in Claim 6 under relative stringent conditions (1.0×SSC, 0.1% SDS, 65° C.), reference being made to T. Maniatis, A laboratory Manual (CSH)

d) a derivative of a DNA sequence defined in a), b) or c), or e) a DNA sequence which codes for a mature xylanase or a signal peptide or a leader peptide thereof and which is degenerate within the meaning of the genetic code with respect to a DNA sequence of a), b) or c).

Also, the invention comprises a vector, which is characterized by the fact that it comprises the recombinant DNA sequence according to the invention.

A preferred embodiment of the vector according to the invention is characterized by the fact that the promoter is the *Aspergillus oryzae* takaamylase promoter and/or the xylanase gene is isolated from EC 3-2, and/or the terminator is the *Aspergillus oryzae* AMG terminator, preferably pHD450. The construction of pHD450 is explained on page 18, lines 3–10.

Also, the invention comprises a transformed host, which is characterized by the fact that it contains the vector according to the invention.

A preferred embodiment of the transformed host according to the invention is characterized by the fact that it is an Aspergillus strain.

A preferred embodiment of the transformed host according to the invention is characterized by the fact that it is a strain belonging to the species *Aspergillus aculeatus, Aspergillus niger, Aspergillus oryzae* or *Aspergillus awamori*.

A preferred embodiment of the transformed host according to the invention is characterized by the fact that it is a microorganism, which in its non-transformed condition does not produce xylanase or only produces xylanase in insignificant amounts, preferably Bacillus sp., *E. coli* or *S. cerevisiae*.

Also, the invention comprises a method for production of xylanase, which is characterized by the fact that the method utilizes a transformed host according to the invention.

Also, the invention comprises the xylanase, produced by means of the method according to the invention.

Also, the invention comprises an agent containing the xylanase according to the invention, preferably in the form of a non-dusting granulate, a stabilized liquid or a protected enzyme, whereby the xylanase comprises at least 10%, preferably at least 30% of the total enzyme protein.

A preferred embodiment of the agent according to the invention is characterized by the fact that the proportion between the xylanase activity and the cellulase activity, as expressed by the ratio between the xylanase activity in EXU/g and the cellulase activity in ECU/g has a value above 10, preferably above 30, most preferably above 100. The cellulase activity unit ECU is defined in AF 302-1.

A preferred embodiment of the agent according to the invention is characterized by the fact that it contains a xylanase activity of at least 10 EXU/mg of enzyme protein, preferably at least 100 EXU/mg of enzyme protein, more preferably at least 300 EXU/mg of enzyme protein.

Also, the invention comprises a use of the agent according to the invention, the use being characterized by the fact that the agent is used for xylan degradation.

A preferred embodiment of the use according to the invention is characterized by the fact that the use is related to chemical pulp or recycle paper pulp before or as part of bleaching, preferably at a pH value above 7.

A preferred embodiment of the use according to the invention is characterized by the fact that the use is related to production of bread, which contains wheat flour.

A preferred embodiment of the use according to the invention is characterized by the fact that the use is related to animal feed.

The xylanase according to the invention can be produced in the following manner.

Xylanase was produced by cultivating *Humicola insolens* DSM 1800, as described in U.S. Pat. No. 4,435,307, Example 6 from the beginning thereof to column 11, line 29. The freeze dried powder was diluted with water to a dry matter content of 10%, and pH was lowered to 2.3 with 10% HCl. The mixture was left alone at 22° C. for 50 minutes, and subsequently pH was increased to 8.0 with NaOH. Then a salt precipitation with 250 g of $Na_2SO_4$ per kg of liquid at pH 5.0 was carried out. The salt cake was redissolved and then concentrated and washed by ultrafiltration. Finally the preparation was frozen down.

In a 12% dry matter solution the xylanase preparation exhibited the following enzyme activities: 444 CSU/ml and 144 EXU/ml. CSU is the cellulase activity unit, vide AF 267.

This preparation was further purified by batch ion exchange with DEAE Sephadex A-50 (Pharmacia), concentration by AMICON ultrafiltration, gel filtration on Sephacryl S-200 (Pharmacia), and cation exchange with high load S-Sepharose (Pharmacia).

It was found that the xylanase did not exhibit any detectable cellulase side activity. Thus, the purified xylanase product showed a cellulase activity of less than 0.1 CSU/mg protein and a xylanase activity higher than 350 EXU/mg protein. The purified xylanase product shows only one SDS-PAGE band with molecular weight 22 kD. The pI was determined to 8.5 by isoelectric focusing.

The antibody reactive with this purified xylanase product was produced in the following manner. Antiserum against the purified xylanase was raised by immunizing rabbits according to the procedure described by N. Axelsen et al.: A Manual of Quantitative Immunoelectrophoresis, Blackwell Scientific Publications, 1973, Chapter 23. A purified immunoglobulin was obtained from the antiserum by salt precipitation (($NH_4$)$_2SO_4$), followed by dialysis and ion exchange chromatography on DEAE-Sephadex. Immunochemical characterization of the purified xylanase was conducted by rocket immunoelectrophoresis (N. Axelsen et al., Chapter 2,). With the antibody indicated above the purified xylanase showed a single arch moving against the cathode in rocket immunoelectrophoresis.

In order to characterize the xylanase chemically the total amino acid composition was determined by acid hydrolysis according to Moore and Stein (1963), Methods Enzymol. 6, 819–831, and by qualitative and quantitative determination of the amino acids in the hydrolysis mixture according to Heinrikson and Meredith (1984), Anal. Biochem. 136, 65–74 (derivatisation) and Edelhoch (1967), Biochemistry 6, 1948–1954 (tryptophan determination). The last indicated literature reference describes the spectrophotometric determination of the tryptophan content. The following amino acid composition was found.

| | Composition (mole per cent) | Standard deviation | Approximated composition according to molecular weight | Maximum number of amino acid residues | Minimum number of amino acid residues |
|---|---|---|---|---|---|
| Asx (B) | 13.16 | 0.75 | 25 | 27 | 24 |
| Glx (Z) | 12.94 | 0.37 | 25 | 25 | 24 |
| Ser (S) | 6.07 | 0.16 | 12 | 12 | 11 |
| Gly (G) | 14.01 | 0.48 | 27 | 28 | 26 |
| His (H) | 2.49 | 0.10 | 5 | 5 | 5 |
| Arg (R) | 4.91 | 0.33 | 9 | 10 | 9 |
| Thr (T) | 7.19 | 0.09 | 14 | 14 | 14 |
| Ala (A) | 2.94 | 0.23 | 6 | 6 | 5 |
| Pro (P) | 4.16 | 0.13 | 8 | 8 | 8 |
| Tyr (Y) | 9.77 | 0.21 | 19 | 19 | 18 |
| Val (V) | 6.10 | 0.38 | 12 | 12 | 11 |
| Met (M) | 0.93 | 0.07 | 2 | 2 | 2 |
| Cys (C) | 0.00 | 0.00 | 0 | 0 | 0 |
| Ile (I) | 2.68 | 0.12 | 5 | 5 | 5 |
| Leu (L) | 2.15 | 0.05 | 4 | 4 | 4 |
| Phe (F) | 3.50 | 0.07 | 7 | 7 | 7 |
| Lys (K) | 2.09 | 0.05 | 4 | 4 | 4 |
| Trp (W) | 4.89 | 0.10 | 9 | 10 | 9 |
| Total | 99.98 | | 193 | 198 | 186 |

The N-terminal amino acid sequence of the purified xylanase was found to be

```
1              5                  10                 15        (SEQ ID NO. 6)
Gln—Val—Thr—Pro—Asn—Ala—Glu—Gly—Trp—His—Asn—Gly—Tyr—Phe—Tyr—
                                                       55
```

Also, after enzymatic degradation with chymotrypsin three peptides are sequenced, whereby one of these is determined as a side sequence (ss) during the sequencing of another peptide:

Chymo-22    Asn-Thr-Gly-Asn-Phe-Val-Gly-Gly-Lys-Gly-Trp-Asn-Pro-Gly-Thr-Gly-Arg-Thr-Ile-Asn-Tyr-    (SEQ ID NO. 1)

Chymo-22    Thr-Arg-Asn-Pro-Leu-Val-Glu-Tyr-Tyr-    (ss) (SEQ ID NO. 2)

Chymo-24:   Ser-Trp-Trp-Ser-Asp-Gly-Gly-Gly-Gln-Val-Gln-Tyr-  (SEQ ID NO. 3)

After chemical degradation with CNBr followed by enzymatic degradation with pepsin two peptides are sequenced.

CNBr/Pep-16:    Val-Ser-Thr-Arg-Tyr-Asn-Gln-Pro-Ser-Ile-Asp-Gly-Thr-Arg-Thr-Phe-Gln-Gln-Tyr-Trp-Ser-Ile-Arg-Lys-  (SEQ ID NO. 4)

CNBr/Pep-23:    Tyr-Val-Ile-Glu-Ser-Tyr-Gly-Thr-Tyr-Asn-Pro-Gly-Ser-Gln-Ala-Gln-Tyr-Lys-Gly-Thr-Phe-Tyr-Thr-Asp-Gly-Asp-Gln-Tyr-Asp-  (SEQ NO. 5)

It has been found that the xylanase according to the invention exhibits a weak homology to prior art xylanases, e.g. xylanases producible from *Schizophyllum communue*, *Bacillus pumilus* and *Bacillus subtilis*.

The invention will be illustrated by the following examples.

Example 1 illustrates the selection of the xylanase producing gene and production of the xylanase by means of a genetic modified host organism. Example 2 illustrates the production in pilot plant of the xylanase and purification of the xylanase. Example 3 illustrates the use of the xylanase as a bleach booster during paper pulp production and Example 4 illustrates the use of the xylanase as a baking agent.

EXAMPLE 1

Media

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

Oat spelt xylan overlayer gel: 1% agarose, 1% oat spelt xylan (Sigma Chemical Company) in Tris-maleic buffer, pH 7. The gel was boiled and then cooled to 55° C. before the overlayer is poured onto agar plates.

FG-4-Agar: 35 g/l agar, 30 g/l Soy bean meal, 15 g/l maltodextrin (Glucidex 6), 5 g/l Bacto pepton, pH 7. Autoclaved 40 min at 121° C.

FG-4 medium: 30 g/l Soy bean meal, 15 g/l maltodextrin (Glucidex 6), 5 g/l Bacto pepton. Autoclaved 40 min at 121° C.

Construction of a yeast expression plasmid

The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Bal1 exonuclease treatment followed by addition of a SphI linker. Finally, an EcoRI linker was added at position −10. After these modifications, the promoter is included in a SphI-EcoRI fragment. Its efficiency compared to the original promoter appears to be unaffected by the modifications. The resulting plasmid pYHD17 is shown in FIG. 1.

Donor organism

*H. insolens*, DSM 1800, grown in a cellulose-rich fermentation medium with agitation to ensure sufficient aeration.

Isolation of mRNA

Total RNA was isolated from approximately 7 g of mycelium. The mycelium was frozen in liquid nitrogen and ground in a mortar with 1 g of quartz sand to a consistency of flour. The RNA was extracted with guanidinium thiocyanate and centrifuged through CsCl essentially as described in Sambrook et al., 1989, op. cit. Poly A RNA was isolated from total RNA by chromatography on oligo dT cellulose.

cDNA synthesis cDNA synthesis was carried out by means of a cDNA synthesis kit from Invitrogen according to the manufacturer's specifications. The DNA was adapted to the expression vectors by addition of a BstxI linker (Invitrogen) and size fractionated on an agarose gel. Only DNA larger than 5–600 bp was used in the library construction. The adapted cDNA was ligated into an appropriate yeast expression vector cut with BstxI. Following test ligations (in order to determine the size of the library) the library was plated onto 50 agar plates amounting to approximately 5000 transformants per plate. To each plate containing approximately 5000 individual clones was added 3 ml of medium. The bacteria were scraped off, 1 ml glycerol was added, and stored at −80° C. as 50 pools. The remaining 2 ml were used for DNA isolation. If the amount of DNA was insufficient to give the required number of yeast transformants (see below), large scale DNA was prepared from 500 ml medium (TB) inoculated with 50 μl-80° C. bacterial stock propagated over night. DNA was isolated from 20 individual clones from the library and subjected to analysis for cDNA insertion. The insertion frequency was found to be >90% and the average insert size was approximately 1400 bp.

Transformation of yeast

The yeast strain used was yNG231. (MAT alpha, leu2, ura3-52, his4-539, pep4-delta 1, cir+). One colony was grown at 30° C. overnight in 10 ml of YPD. 10, 30, and 60 μl of this culture were added to 3 shaker flasks containing 100 ml YPD, and incubated with shaking overnight at 30° C. The culture with an $OD_{600}$ closest to 0.3–0.4 was selected. The cells were harvested in 50 ml tubes in a Beckman centrifuge (speed 6, 10 minutes), the cells were resuspended in 2×5 ml $H_2O$, centrifuged as described above, resuspended in 5 ml buffer containing 0.1M LiAc, 10 mM Tris-Cl, 1 mM EDTA, pH 7.5, and centrifuged again. The cells were resuspended in 500 μl of the above buffer and incubated for 60 minutes at 30° C. 250 μg carrier DNA (sterile salmon-sperm DNA 10 mg/ml, see below) was added and aliquots of 100 μl were prepared. The DNA to be transformed (approx. 5 μg) was added to the 100 μl aliquot, mixed gently, and incubated for 30 minutes at 30° C. 700 μl 40% PEG 4000, 0.1M LiAc, 10 mM Tris-Cl, 1 mM EDTA, pH 7.5 was added, and incubation was continued for 60 minutes at 30° C. The transformation mixture was subjected to heat shock for 5 minutes at 42° C., spun briefly in a micro centrifuge, resuspended in 100–200 μl $H_2O$, and plated on SC plates without uracil, followed by incubation for three days at 30° C.

Preparation of carrier DNA 100 mg salmon-sperm DNA was weighed out and dissolved overnight in 10 ml 10 mM Tris-Cl, 1 mM EDTA, pH 7,5 (TE). The solution was then sonicated in a plastic container in ice water until it was no longer viscous. The solution was then phenol extracted and EtOH precipitated, and the pellet was washed and resuspended in 5 ml TE. The suspension was EtOH precipitated, and the pellet was washed and resuspended in 5 ml TE. The $OD_{260}$ was measured, and the suspension was diluted with TE to 10 mg/ml.

Screening of yeast

As described above DNA from the Humicola library, pools 1–10, was transformed into yeast, and plates containing 20–25,000 colonies were obtained from each pool. The colonies were scraped off and stored in glycerol at −80° C.

Yeast cells from the library were spread onto YNB agar to a total of about 400,000 colonies. The number of colonies per plate varied from 50 to 500. After 4 or 5 days of growth, the agar plates were replica plated onto a set of SC—H agar plates. These plates were then incubated for 2–4 days at 30° C. before the agar plates were overlayered with a oat spelt xylan overlayer gel for the detection of xylanase. After incubation overnight at 40° C., enzyme reactions were visualised with Congo Red. 10–15 ml of a 0.1% solution of Congo Red was poured onto the overlayer and removed after 10–20 min. The plates were then washed once or twice by pouring 10–15 ml of 2M NaCl onto the plates. The NaCl solution was removed after 15–25 min. Xylanase-positive colonies identified on the plates overlayers as colourless or pale red clearing zones on a red background.

Cells from enzyme-positive colonies were spread for single colony isolation on agar, and an enzyme-producing single colony was selected for each of the xylanase-producing colonies identified.

Characterization of xylanase positive clones

Each of the 147 of the xylanase-producing colonies were isolated. Some of these colonies were inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 µl 5M KOAc was added, and the suspension was incubated on ice for at least 60 minutes and spun for 15 minutes at full speed. The supernatant is was transferred to a fresh tube which was filled with EtOH (room temperature) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into *E. coli* by standard procedures. Two *E. coli* colonies were isolated from each of the transformations and analysed with the restriction enzymes HindIII and XbaI which excised the DNA insert. DNA from one of these clones was retransformed into yeast and rescreened for enzyme activity.

The DNA sequences of several of the positive clones were partially determined. Based on the DNA sequence, 15 clones were classified as the same family, the sequence of this xylanase family showed full homology with the amino acid sequence of the purified xylanase according to the invention. A partial DNA sequence is SEQ ID NO: 7.

A strain of *E. coli* containing the xylanase HindIII/XbaI cDNA fragment in pYES2 was deposited in DSM on Mar. 18, 1992, as DSM 6995. The xylanase cDNA fragment was isolated from one of the clones by cleavage with HindIII/XbaI. The HindIII/XbaI fragment was purified by agarose gel electrophoresis electroeluted and made ready for ligation reactions. The cDNA fragment is ligated to HindIII/XbaI digested pHD414 (see below) to generate pHD 450 in which the cDNA is under transcriptional control of the TAKA promotor from *Aspergillus oryzae* and the AMG terminator from *Aspergillus niger*.

After amplification of the DNA in *E. coli* the plasmid was transformed into *Aspergillus oryzae* as described as follows.

Construction of an Aspergillus expression vector

Figure 2:
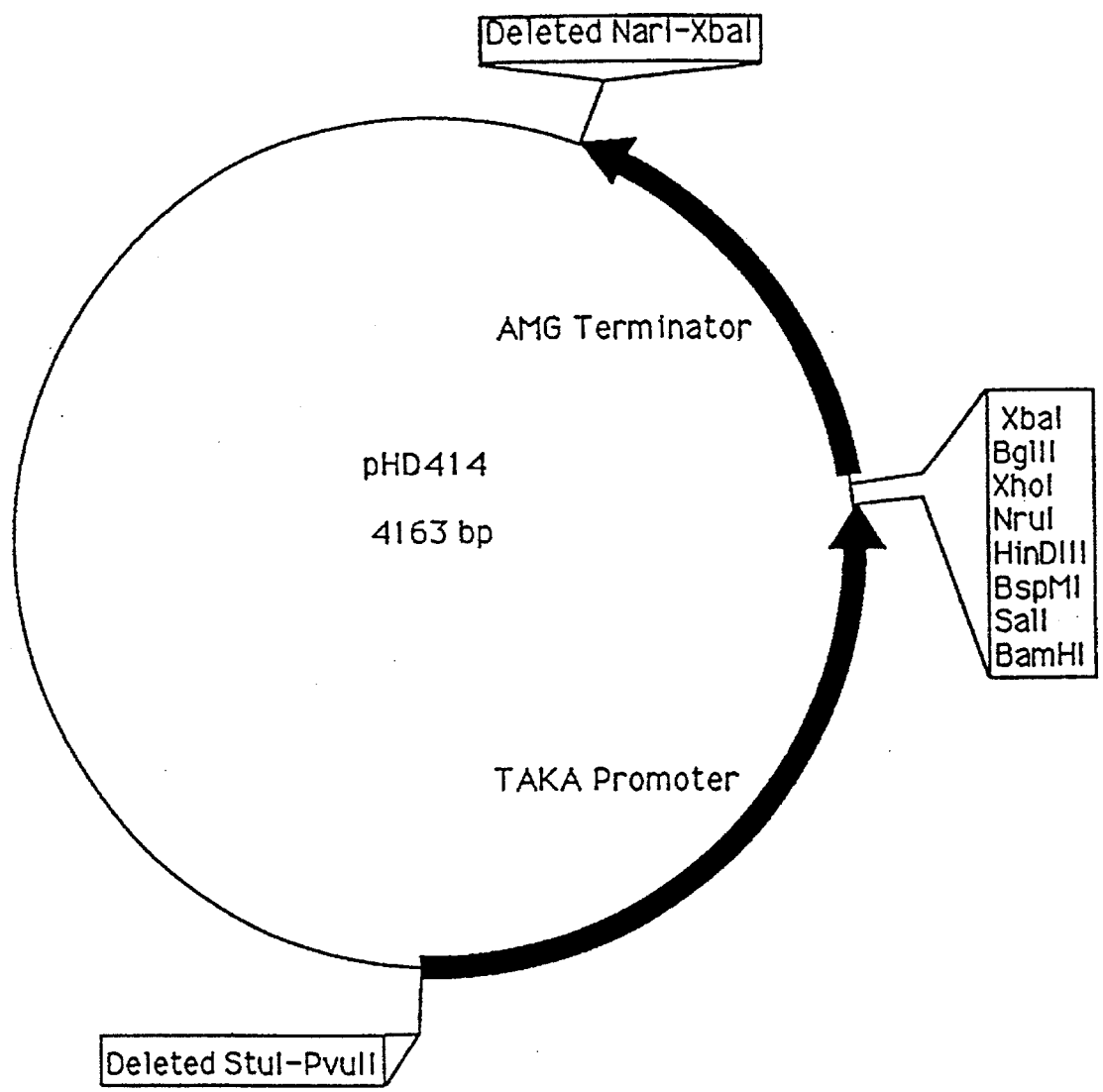
FIG. 2 depicts a functional map of the expression plasmid pHD414 featuring a multiple cloning site positioned between the *Aspergillus oryzae* TAKA amylase promoter and the *Aspergillus niger* glucoamylase terminator.

The vector pHD414 (FIG. 2) is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated, resulting in pHD414. FIG. 2 is a map of plasmid pHD414, wherein "AMG Terminator" indicates the *A. niger* glucoamylase terminator, and "TAKA Promoter" indicates the *A. oryzae* TAKA amylase promoter.

Transformation of *Aspergillus Oryzae*

100 ml of YPD (Sherman et al., Methods in Yeast Genetics, Cold Spring Harbor Laboratory, 1981) is inoculated with spores of *A. oryzae* or and incubated with shaking at 37° C. for about 2 days. The mycelium is harvested by filtration through miracloth and washed with 200 ml of 0.6M MgSO$_4$. The mycelium is suspended in 15 ml of 1.2M MgSO$_4$. 10 mM NaH$_2$PO$_4$, pH=5.8. The suspension is cooled on ice and 1 ml of buffer containing 120 mg of Novozym® 234 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the MgSO$_4$ cushion. 2 volumes of STC (1.2M sorbitol, 10 mM Tris-HCl, pH=7.5. 10 mM CaCl$_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM CaCl$_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove, see Biochem. Biophys. Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Expression of the xylanase in Aspergillus 11 transformants were obtained and inoculated and maintained on YPG-agar. Each of the 8 selected transformants were inoculated from YPG-agar slants on 500 ml shake flask with 150 ml FG-4 media. After 4 days of fermentation with sufficient agitation to ensure good aeration, the culture broths were centrifuged for 10 minutes at 2000 g and the supernatants were analyzed. The best yielded 72 EXU/ml. There is no background from the untransformed host strain. This strain is designated Axy40/8.

EXAMPLE 2

The strain Axy40/8 was fermented in a pilot plant scale in the following way.

An agar substrate with the following composition was prepared in a Fernbach flask:

| Sucrose | 30 g/l |
|---|---|
| $KH_2PO_4$ | 1 g/l |
| $NaNO_3$ | 3 g/l |
| $MgSO_4, 7H_2O$ | 0,5 g/l |
| $FeSO_4, 7H_2O$ | 0,01 g/l |
| KCl | 0,5 g/l |
| Agar | 25 g/l | pH was adjusted to between 6.4–6.5, autoclaved for 20 minutes at 121° C.

The Fernback flask was inoculated with a spore suspension and cultivated 5 days at 30° C.

A substrate with the following composition was prepared in a 500 liter seed fermenter:

| Yeast extract, 50% | 6 kg |
|---|---|
| Potato starch | 9 kg |
| $CaCO_3$ | 0,15 kg |
| Pluronic L61 | 150 ml |
| Termamyl ® 60 (L)* | 9 g |

*) Termamyl is an alpha-amylase obtainable from Novo Nordisk A/S

Tap water was added to a total volume of around 225 liters. pH was adjusted to around 6.5 with $H_3PO_4$.

The temperature was raised from 60° to 90° C. in 30 minutes, held for 30 minutes at 90° C., before the substrate was sterilized in the seed fermenter for 1.5 hour at 121° C. Final volume before inoculation was around 300 liters.

The Fernbach flask spore suspension was transferred to the seed fermenter. Seed fermentation conditions were:

Fermenter type: Conventional aerated-and agitated fermenter with a height/diameter ratio of around 2.3.

| Agitation: | 250 rpm |
|---|---|
| Aeration: | 300 normal liter air per minute |
| Temperature: | 34° C. |
| Time: | around 24 hours |

Around 35 hours after inoculation 150 liters was transferred from the seed fermenter to the main fermenter.

A substrate with the following composition was prepared in a 2500 liter main fermenter:

| $MgSO_4, 7H_2O$ | 2.6 kg |
|---|---|
| $KH_2PO_4$ | 2.6 kg |
| $K_2SO_4$ | 3.9 kg |
| Trace metal solution | 650 ml |
| Potato starch | 39.0 kg |
| Yeast extract, 50% | 28.6 kg |
| Urea | 5.2 kg |
| Citric acid | 1.053 kg |
| Pluronic L61 | 650 ml |
| Termamyl ® 60 L | 39 g |

The trace metal solution has the following composition:

| $ZnSO_4, 7H_2O$ | 14.3 g/l |
|---|---|
| $CuSO_4, 7H_2O$ | 2.5 g/l |
| $NiCl_2, 6H_2O$ | 0.5 g/l |
| $FeSO_4, 7H_2O$ | 13.5 g/l |
| $MnSO_4, H_2O$ | 8.5 g/l |
| Citric acid, monohydrate | 3.0 g/l |

Tap water was added to a total volume of around 900 liters. pH was adjusted to 6.5 with $H_3PO_4$. The temperature was raised from 60° to 90° C. in 30 minutes, held for 30 minutes at 90° C. Then pH was adjusted to 4.5 before the substrate was sterilized in the main fermenter for 1.5 hours at 123° C. Final volume before inoculation was around 1300 liters.

Then 150 liters of seed culture was added.

Fermentation conditions were:

Fermenter type: Conventional aerated and agitated fermenter with a height/diameter ratio of around 2.7.

| Agitation: | 250 rpm (two turbine impellers) |
|---|---|
| Aeration: | 1500 normal liter air per minute, rising to 1700 Nl/min at 130 hours. |
| Temperature: | 34° C. |
| Time: | around 130 hours |

After 25 hours into the fermentation a maltodextrin solution was added aseptically to the main fermenter at a rate increasing from 1 l/hour to 4 l/hour in 12 hours. The dextrin solution was prepared with the following composition in a 550 liter feed tank:

| Potato starch | 184 kg |
|---|---|
| Biotin | 0.04 g |
| Thiamin | 0.4 g |
| Citric acid | 0.2 kg |
| Pluronic L61 | 200 ml |
| Termamyl ® 60L | 360 ml |

Tap water was added to a total volume of around 300 liters. The temperature was held at 90° C. for 60 minutes before the substrate was sterilized in the dosing tank for 1.5 hours at 123° C. Final volume before start of dosage was around 400 liters.

After 25 hours of fermentation pH was controlled at 7.3–7.4 by $NH_3$.

After around 130 fermentation hours the fermentation process was stopped. The around 1850 liters of culture broth were cooled to around 5° C. and the enzymes were recovered according to the following method.

The culture broth was centrifuged at pH 7 and the centrifugate was filtered on a Seitz filter sheet (type Supra EKS Neu) using Hyflo Super-Cell diatomaceous earth as a filter aid. The pH in the filtrate was adjusted to 4.7 and the filtrate was concentrated to a dry matter content of 5% using ultrafiltration. Further concentration to a dry matter content of 30% was carried out by evaporation. The pH in the concentrate was adjusted to 6.5 and the concentrate was filtered on a frame filter using Hyflo Super-Cell as filter aid and germ filtered on a Seitz filter sheet (type Supra EKS Neu).

This concentrate is identified later in this specification as preparation 1. Preparation 1 exhibits a xylanase activity of 533 EXU/g.

Preparation 1 was purified as follows.

Totally 200,000 EXU was precipitated with 25% ammonium sulfate. The precipitate was solubilized in 500 ml of water and washed on an Amicon ultrafiltration cell with a membrane GR90PP from Dow Danmark A/S. The conductivity was reduced to 1.7 mS. The yield was 150,000 EXU. The pH was adjusted to 5.0 and the sample filtered through a 0.45 micron filter; yield 100,000 EXU. The sample was treated by cation exchange chromatography by means of 200 ml S-Sepharose fast flow column chromatography and a buffer containing 20 mM sodium acetate with pH 5.0. The xylanase bound to the column at this pH. The xylanase was eluted using a linear gradient containing 1M sodium chloride in the same buffer. Totally 75,000 EXU was recovered in 160 ml with $E_{280}$ 4.1 which corresponds to 114 EXU per $E_{280}$.

For peptide mapping and measurement of the specific activity and characterization the xylanase is obtained in high purity by a final purification step. By means of size chromatography Superdex 75 a small portion of the xylanase has been highly purified. The purified xylanase has a single band in SDS-PAGE with a molecular weight of 22 kD, and a single band in isoelectric focusing by means of Pharmacia IEF gels with a pI of 8.2.

The native and the cloned xylanase according to the invention purified as described above, react equally with rabbit serum raised against purified native xylanase. By use of rocket immunoelectroforesis both enzymes on an equal EXU basis give rise to the same immune precipitate.

By use of the EXU method the activity of the purified xylanase on colored xylan is 130 EXU per $E_{280}$ or 450 EXU per mg protein. The extinction coefficient is 3.5 $E_{280}$.

EXAMPLE 3

In this example the prior art *B. pumilus* xylanase has been compared with the xylanase according to the invention. Preparation 1 described in Example 2 was used for the comparison. On a softwood pulp, it was seen that the xylanase according to the invention gave a significantly better bleach boosting effect.

Xylanase according to the invention: *H. insolens* xylanase, liquid preparation, 533 EXU/g Prior art xylanase: *B. pumilus* xylanase liquid preparation, 1070 EXU/g Pulp Unbleached softwood from a Swedish mill. The pulp has been washed, air dried, and stored at <5° C. in a cool room.

The pulp was soaked for >12 hours in water whereafter it was pulped in a laboratory pulper at 1% DS, 10,000 reversions.

TABLE 1

| Data for the pulp measured after storage | |
|---|---|
| Pulp data measured | Softwood |
| Kappa No. | 25.8 |
| pH | 7.35 |
| Dry matter (%) | 97.0 |
| ISO brightness (%) | 28.3 |

Two bleaching trials were performed, each consisting of the following two stages:
 1) Enzyme treatment
 2) (D50C50)E delignification
Laboratory bleaching conditions
 Enzyme
  50° C., pH 8.0 (Britton-Robinson buffer). Treatment time and dosage to be described later under the heading "Enzyme treatment".

(D50C50)
45 minutes, 40° C., 5% DS, final pH: 1.9–2.9.
aCL-multiples: 0.15, 0.19, 0.23, 0.27
E
60 minutes, 60° C., 12% DS, final pH: 10.6–12.2.

The NaOH dosage is calculated from the chlorine chemicals applied in the delignification stage as

[0.5·(kg $Cl_2$/ton+$ClO_2$/ton)+3] kg/ton

The bleaching stages were carried out in plastic bags heated in water baths. The bags were kneaded by hand at regular intervals.

Enzyme treatment

Two samples of pulp were treated in the same enzyme stage: one with the xylanase according to the invention, and the other with the prior art xylanase. The treatment time was 3 hours and the dosage was 1000 EXU/kg. Afterwards, the pulp was washed thoroughly with cold water. A third sample—the control—was given the same treatment, but without enzyme addition.

A significant difference between the two enzymes was seen in this experiment.

The Kappa numbers and absorbances measured after enzyme treatment are presented in Table 2.

TABLE 2

| Data measured after the enzyme stage | | | |
|---|---|---|---|
| | Control | Xylanase according to the invention | Prior art xylanase |
| Kappa no. | 24.3 | 23.0 | 23.7 |
| Abs. 280 nm | 0.31 | 1.36 | 1.32 |

(D50C50)E delignification

From each of the three samples, four portions each of about 17 g of pulp were delignified with different dosages of active chlorine. Afterwards, the Kappa nos. and the ISO brightness values were measured. The results are shown in Table 3.

From Table 3 it appears that the *H. insolens* xylanase according to the invention provides a markedly lower Kappa no. and a better brightness than the prior art xylanase. Even if it appears from Table 3 that the Kappa no. in relation to the xylanase according to the invention is only slightly smaller than the Kappa no. in relation to the prior art xylanase, this slight difference corresponds to a much larger and significant saving of used active chlorine.

TABLE 3

| Kappa nos. and brightness after enz(D50C50)E delignification of the pulp | | | | | |
|---|---|---|---|---|---|
| aCl multiple* | | 0.15 | 0.19 | 0.23 | 0.27 |
| kg of aCl/ton | | 36.5 | 46.2 | 56.0 | 65.7 |
| Control | Kappa no. | 8.48 | 6.33 | 4.55 | 3.89 |
| | % ISO | 36.1 | 40.8 | 45.0 | 47.5 |
| Xylanase according to the invention | Kappa No. | 7.22 | 4.92 | 3.88 | 3.03 |
| | % ISO | 39.1 | 44.0 | 47.9 | 51.5 |
| Prior art xylanase | Kappa No. | 7.54 | 5.66 | 4.07 | 3.28 |
| | % ISO | 38.7 | 42.0 | 46.5 | 51.1 |

*Multiple on Kappa no. of control

For the pulp used in this experiment it can be concluded that the xylanase according to the invention will generate a higher bleach boosting effect than the prior art xylanase.

EXAMPLE 4

This example illustrates the use of the xylanase according to the invention as a baking agent.

Xylanase (the designation pentosanase is commonly used in the baking industry) is used as a baking agent for wheat bread for several purposes:

dough development
improving dough elasticity and stability
increasing bread volume
improving crumb structure
anti-staling Preparation 1 has been tested in wheat bread and it has very good effect on bread quality. This enzyme has sufficient dough softening effect. Addition of 43–150 FXU of preparation 1 increases the volume of rolls by 5–20% and crumb structure become more uniform and crumb is softer than bread without enzyme. It has a better effect in comparison to the commercial products. The xylanase activity unit FXU is defined in AF 293.6.

The prior art xylanase baking agents comprise several enzymatic activities, whereas the baking agent according to the invention easily can be produced with a very low content of enzymatic activities other than the xylanase activity. Thus, by use of the baking agent according to the invention bakery products with more constant characteristics from one baking operation to the next baking operation can be obtained.

Recipe and baking process
The basic recipe in this example is:

| | |
|---|---|
| wheat flour | 1000 g |
| salt | 16 g |
| sugar | 16 g |
| yeast | 50 g |
| water | 590 g |
| enzyme | |

The ingredients were mixed by a spiral dough-kneading machine. The dough was then kneaded for 2 minutes, at low speed and 5 minutes, at high speed. The dough temperature was approx. 26°–28° C. After 10 minutes of resting, the dough was divided and formed to 30 rolls and 1 loaf. After a proofing time of 45 minutes for rolls and 40 minutes for loaf at 33° C., 80% RH, the rolls and the loaf were baked at 220° C. for 15 minutes, and 30 minutes, respectively.

In prep. 1 without amylase activity the amylase activity produced by the host organism is separated from the xylanase by means of conventional chromatographic techniques.

The roll and loaf volumes are measured using the traditional rape seeds method. The measured values are then recalculated to relative index.

The crumb softness is measured on a SMS-Texture Analyzer. A plunger with a diameter of 25 mm is pressed on the middle of a 11 mm thick slice of bread, the force needed for the plunger to depress the crumb 3 mm with a speed of 3.3 mm/s is recorded, and it is expressed as the crumb softness. The value is then recalculated to a relative index related to the reference sample which by definition has an index of 100. The lower the index for crumb softness, the softer is the crumb.

The characters for dough development and crumb structure are given according to visual evaluation: + means that the dough is normal, and that the crumb is also normal with coarse structure, and ++ means that the dough is softer than the reference and more elastic, and that the crumb structure is uniform and silky.

Pentopan™, a commercial preparation available from Novo Nordisk A/S, is a prior art baking agent which contains different xylanases from *H. insolens* and also other *H. insolens* enzyme activities. It appears from the above that the xylanase according to the invention has a better performance than the prior art baking agent as it provides larger volume and softer crumb. The most important baking advantage in relation to the xylanase according to the invention, in comparison to the prior art xylanase is the fact that the xylanase according to the invention can be used as a baking agent with practically no side activities, and thus is able to generate bread with very uniform properties from batch to batch.

| | Results | | | | | | |
|---|---|---|---|---|---|---|---|
| | FXU/kg flour | Dough development | V-rolls index | V-loaf index | Crumb structure | Softness | |
| Reference | 0 | + | 100 | 100 | + | 100 | 100 |
| Prep. 1 | 43 | ++ | 106 | 105 | ++ | 87 | 66 |
| | 130 | ++ | 115 | 106 | + | 85 | 69 |
| Prep. 1 without amylase activity | 75 | ++ | 108 | 103 | ++ | 79 | 88 |
| | 151 | ++ | 116 | 104 | +(+) | 94 | 83 |
| Pentopan | 122 | ++ | 108 | 101 | ++ | 82 | 94 |
| | 427 | ++ | 111 | 105 | + | 96 | 82 |

We claim:
1. An isolated xylanase endogenous to a *Humicola insolens* strain, which has the following partial amino acid sequences
 a. Asn-Thr-Gly-Asn-Phe-Val-Gly-Gly-Lys-Gly-Trp-Asn-Pro-Gly-Thr-Gly-Arg-Thr-Ile-Asn-Tyr- (SEQ ID NO: 1),
 b. Thr-Arg-Asn-Pro-Leu-Val-Glu-Tyr-Tyr- (SEQ ID NO: 2),
 c. Ser-Trp-Trp-Ser-Asp-Gly-Gly-Gln-Val-Gln-Tyr- (SEQ ID NO: 3),
 d. Val-Ser-Thr-Arg-Tyr-Asn-Gln-Pro-Ser-Ile-Asp-Gly-Thr-Arg-Thr-Phe-Gln-Gln-Tyr-Trp-Ser-Ile-Arg-Lys- (SEQ ID NO: 4),
 e. Tyr-Val-Ile-Glu-Ser-Tyr-Gly-Thr-Tyr-Asn-Pro-Gly-Ser-Gln-Ala-Gln-Tyr-Lys-Gly-Thr-Phe-Tyr-Thr-Asp-Gly-Asp-Gln-Tyr-Asp- (SEQ ID NO: 5), and
 f. Gln-Val-Thr-Pro-Asn-Ala-Glu-Gly-Trp-His-Asn-Gly-Tyr-Phe-Tyr- (SEQ ID NO: 6).

2. The xylanase according to claim 1, wherein the strain is *Humicola insolens*, DSM 1800.

3. The xylanase according to claim 1, wherein the xylanase has an isoelectric point of 7.5–9.5.

4. The xylanase according to claim 3, wherein the xylanase has an isoelectric point of 8.0–8.5.

5. The xylanase according to claim 4, wherein the xylanase has an isoelectric point of 8.2.

6. The xylanase according to claim 1, wherein the xylanase has a pH optimum of 5.5–7.5.

7. The xylanase according to claim 1, wherein the xylanase has a molecular weight of 22 kDa.

8. The xylanase according to claim 1, wherein the xylanase exhibits a specific activity above 330 EXU/mg of protein.

9. A xylanase according to claim 1 in the form of a non-dusting granulate, a stabilized liquid or a protected enzyme.

10. The xylanase according to claim 9, wherein the ratio of xylanase activity in EXU/g to cellulase activity in ECU/g is above 10.

11. The xylanase according to claim 10 which contains a xylanase activity of at least 10 EXU/mg of enzyme protein.

12. An isolated xylanase which is encoded by a DNA sequence endogenous to a strain of the genus Humicola which comprises the following partial DNA sequence

```
            1              5                   10                 15
          ATG GTC TCG CTC AAG TCT GTC CTC GCG GCC GCC ACG GCT GTG AGC
                          20                  25                 30
          TCT GCC ATT GCT GCC CCT TTT GAC TTC GTT CCT CGG GAC AAC TCG
                          35                  40                 45
          ACG GCC CTT CAG GCT CGC CAG GTG ACC CCC AAC GCC GAG GGC TGG
                          50                  55                 60
          CAC AAC GGC TAC TTC TAC TCG TGG TGG TCC GAC GGC GGA GGC CAG
                          65                  70                 75
          GTT CAG TAC ACC AAC CTC GAG GGC AGC CGC TAC CAG GTC AGA TGG
                          80                  85                 90
          NNN AAC ACC GGC AAC TTC GTC GGT GGT AAG GGT TGG AAC CCG GGA
                          95                 100                105
          ACC GGC CCC ACG ATC AAC TAC GGC GGC TAC TTC AAC CCC CAG GGC
                         110                 115                120
          AAC GGC TAC CTG GCC GTC TAC GGC TGG ACC NNN AAC CCG CTC GTC
                         125                 130                135
          GAG TAC TAT GTC ATC GAG TCG TAC GGC ACG TAC AAT CCC GGC AGC
                         140                 145                150
          CAG GCT CAG TAC AAG GGC ACA TTC TAT ACC GAC GGC GAT CAG TAT
                         155                 160
          GAC ATC TTT GTG AGC ACC CGT NNN AAC CAG CCC AGC ATC
```

(SEQ ID NO: 7) or a DNA sequence endogenous to a strain of the genus Humicola which hybridizes to the coding region of SEQ ID NO: 7 under the following conditions: 1.0×SSC, 0.1% SDS and 65° C.

13. The xylanase according to claim 12 which is obtained from a *Humicola insolens* strain.

14. An isolated xylanase which is obtained from a *Humicola insolens* strain and has an isoelectric point of 7.5–9.5 and a pH optimum of 5.5–7.5.

15. The xylanase according to claim 14, wherein the xylanase has an isoelectric point of 8.0–8.5.

16. The xylanase according to claim 15, wherein the xylanase has an isoelectric point of 8.2.

17. The xylanase according to claim 14, wherein the xylanase has a molecular weight of 22 kDa.

18. The xylanase according to claim 14, wherein the strain is *Humicola insolens*, DSM 1800.

19. An isolated DNA sequence which codes for the xylanase according to claim 1.

20. A isolated DNA sequence endogenous to a strain of *Humicola insolens*, comprising the following partial DNA sequence

```
 1               5                    10                   15
ATG GTC TCG CTC AAG TCT GTC CTC GCG GCC GCC ACG GCT GTG AGC 20                   25                   30
TCT GCC ATT GCT GCC CCT TTT GAC TTC GTT CCT CGG GAC AAC TCG 35                   40                   45
ACG GCC CTT CAG GCT CGC CAG GTG ACC CCC AAC GCC GAG GGC TGG 50                   55                   60
CAC AAC GGC TAC TTC TAC TCG TGG TGG TCC GAC GGC GGA GGC CAG 65                   70                   75
GTT CAG TAC ACC AAC CTC GAG GGC AGC CGC TAC CAG GTC AGA TGG 80                   85                   90
NNN AAC ACC GGC AAC TTC GTC GGT GGT AAG GGT TGG AAC CCG GGA 95                   100                  105
ACC GGC CCC ACG ATC AAC TAC GGC GGC TAC TTC AAC CCC CAG GGC 110                  115                  120
AAC GGC TAC CTG GCC GTC TAC GGC TGG ACC NNN AAC CCG CTC GTC 125                  130                  135
GAG TAC TAT GTC ATC GAG TCG TAC GGC ACG TAC AAT CCC GGC AGC 140                  145                  150
CAG GCT CAG TAC AAG GGC ACA TTC TAT ACC GAC GGC GAT CAG TAT 155                  160
GAC ATC TTT GTG AGC ACC CGT NNN AAC CAG CCC AGC ATC
```

(SEQ ID NO. 7) or a DNA sequence endogenous to a strain of *Humicola insolens* which hybridizes to the coding region of SEQ ID NO: 7 under the following conditions: 1.0×SSC, 0.1% SDS and 65° C.

21. A vector comprising the DNA sequence according to claim 20.

22. The vector according to claim 21, further comprising an *Aspergillus oryzae* TAKA-amylase promoter and/or an *Aspergillus oryzae* AMG terminator.

23. A host cell which is transformed with the vector according to claim 21.

24. The host cell according to claim 23, wherein the host cell is an Aspergillus cell.

25. The host cell according to claim 24, wherein the host cell is an *Aspergillus aculeatus, Aspergillus niger, Aspergillus oryzae* or *Aspergillus awamori* cell.

26. The host cell according to claim 23, wherein the host cell is a Bacillus sp., *E. coli* or *S. cerevisiae* cell.

27. A method for degrading a xylan, comprising treating the xylan with a xylanase according to claim 1.

28. A method for delignifying a chemical pulp or recycle paper pulp, comprising treating the pulp with a xylanase according to claim 1 at a pH above 7.

29. The method according to claim 28, wherein the pH is 8.

30. A method for preparing a wheat bread, comprising baking a wheat dough in the presence of a xylanase according to claim 1.

31. A method for modifying an animal feed, comprising treating said feed with a xylanase according to claim 1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:1:

```
Asn Thr Gly Asn Phe Val Gly Gly Lys Gly Trp Asn Pro Gly Thr Gly
 1               5                   10                  15

Arg Thr Ile Asn Tyr
            20
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:2:

```
Thr Arg Asn Pro Leu Val Glu Tyr Tyr
 1               5
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
Ser Trp Trp Ser Asp Gly Gly Gly Gln Val Gln Tyr
 1               5                   10
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
Val Ser Thr Arg Tyr Asn Gln Pro Ser Ile Asp Gly Thr Arg Thr Phe
```

```
            1               5                    10                    15

Gln Gln Tyr Trp Ser Ile Arg Lys
                        20
```

( 2 ) INFORMATION FOR SEQ ID NO:5:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
        Tyr Val Ile Glu Ser Tyr Gly Thr Tyr Asn Pro Gly Ser Gln Ala Gln
        1               5                    10                    15

Tyr Lys Gly Thr Phe Tyr Thr Asp Gly Asp Gln Tyr Asp
                        20                  25
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
        Gln Val Thr Pro Asn Ala Glu Gly Trp His Asn Gly Tyr Phe Tyr
        1               5                    10                    15
```

( 2 ) INFORMATION FOR SEQ ID NO:7:

( i ) SEQUENCE CHARACTERISTICS:
        ( A ) LENGTH: 489 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Humicola insolens
        ( B ) STRAIN: DSM 1800

( x i ) SEQUENCE DESCRIPTION: SEQ ID NO:7:

```
ATGGTCTCGC TCAAGTCTGT CCTCGCGGCC GCCACGGCTG TGAGCTCTGC CATTGCTGCC      60
CCTTTTGACT TCGTTCCTCG GGACAACTCG ACGGCCCTTC AGGCTCGCCA GGTGACCCCC     120
AACGCCGAGG GCTGGCACAA CGGCTACTTC TACTCGTGGT GGTCCGACGG CGGAGGCCAG     180
GTTCAGTACA CCAACCTCGA GGGCAGCCGC TACCAGGTCA GATGGNNNAA CACCGGCAAC     240
TTCGTCGGTG GTAAGGGTTG GAACCCGGGA ACCGGCCCCA CGATCAACTA CGGCGGCTAC     300
TTCAACCCCC AGGGCAACGG CTACCTGGCC GTCTACGGCT GGACCNNNAA CCCGCTCGTC     360
GAGTACTATG TCATCGAGTC GTACGGCACG TACAATCCCG CAGCCAGGC TCAGTACAAG      420
GGCACATTCT ATACCGACGG CGATCAGTAT GACATCTTTG TGAGCACCCG TNNNAACCAG     480
CCCAGCATC                                                             489
```